US 9,174,207 B2
Nov. 3, 2015

(12) United States Patent
Mastroianni

(54) PROCESS FOR PRODUCING COMPOUNDS COMPRISING NITRILE FUNCTIONS

(75) Inventor: Sergio Mastroianni, Lyons (FR)

(73) Assignee: INVISTA North America S.a.r.l., Wilmington, DE (US)

( * ) Notice: Subject to any disclaimer, the term of this patent is extended or adjusted under 35 U.S.C. 154(b) by 125 days.

(21) Appl. No.: 13/123,721

(22) PCT Filed: Oct. 5, 2009

(86) PCT No.: PCT/EP2009/062896
§ 371 (c)(1),
(2), (4) Date: Sep. 15, 2011

(87) PCT Pub. No.: WO2010/046226
PCT Pub. Date: Apr. 29, 2010

(65) Prior Publication Data
US 2012/0004440 A1   Jan. 5, 2012

(30) Foreign Application Priority Data

Oct. 21, 2008 (FR) ..................... 08 05821

(51) Int. Cl.
| | | |
|---|---|---|
| B01J 31/24 | (2006.01) |
| B01J 31/18 | (2006.01) |
| B01J 31/12 | (2006.01) |
| B01J 31/14 | (2006.01) |
| B01J 31/22 | (2006.01) |
| C07C 253/10 | (2006.01) |

(52) U.S. Cl.
CPC ............ *B01J 31/1845* (2013.01); *B01J 31/122* (2013.01); *B01J 31/146* (2013.01); *B01J 31/185* (2013.01); *B01J 31/2208* (2013.01); *B01J 31/2409* (2013.01); *C07C 253/10* (2013.01); *B01J 2231/322* (2013.01); *B01J 2523/305* (2013.01); *B01J 2523/41* (2013.01); *B01J 2523/42* (2013.01); *B01J 2523/43* (2013.01); *B01J 2531/847* (2013.01)

(58) Field of Classification Search
CPC ................................................ B01J 2523/847
USPC ........................................................ 558/338
See application file for complete search history.

(56) References Cited

U.S. PATENT DOCUMENTS

| | | | |
|---|---|---|---|
| 3,496,215 A | 2/1970 | Drinkard, Jr. et al. |
| 3,496,217 A | 2/1970 | Drinkard et al. |
| 3,496,218 A | 2/1970 | Drinkard, Jr. et al. |
| 3,631,191 A | 12/1971 | Kane et al. |
| 3,655,723 A | 4/1972 | Drinkard, Jr. |
| 3,694,485 A | 9/1972 | Drinkard, Jr. et al. |
| 3,766,231 A | 10/1973 | Gosser et al. |
| 3,766,237 A | 10/1973 | Chia et al. |
| 3,773,809 A | 11/1973 | Walter |
| 3,864,380 A | 2/1975 | King et al. |
| 4,082,811 A | 4/1978 | Shook, Jr. |
| 4,339,395 A | 7/1982 | Barnette et al. |
| 4,416,825 A | 11/1983 | Ostermaier |
| 4,774,353 A * | 9/1988 | Hall et al. ........... 558/335 |
| 4,874,884 A * | 10/1989 | McKinney et al. ...... 558/338 |
| 5,512,696 A * | 4/1996 | Kreutzer et al. ........ 558/338 |
| 5,693,843 A | 12/1997 | Breikss et al. |
| 5,847,191 A | 12/1998 | Bunel et al. |
| 5,981,772 A | 11/1999 | Foo et al. |
| 6,048,996 A | 4/2000 | Clarkson et al. |
| 6,127,567 A | 10/2000 | Garner et al. |
| 6,153,758 A | 11/2000 | Sannicolo et al. |
| 6,521,778 B1 | 2/2003 | Fischer et al. |
| 6,770,770 B1 | 8/2004 | Baumann et al. |
| 7,084,293 B2 | 8/2006 | Rosier et al. |
| 7,098,358 B2 | 8/2006 | Burattin et al. |
| 7,105,696 B2 | 9/2006 | Burattin et al. |
| 7,442,825 B2 | 10/2008 | Galland et al. |
| 7,470,805 B2 | 12/2008 | Rosier et al. |
| 7,485,741 B2 | 2/2009 | Bourgeois et al. |
| 7,550,407 B2 | 6/2009 | Bartsch et al. |
| 7,612,223 B2 | 11/2009 | Rosier et al. |
| 7,777,068 B2 | 8/2010 | Bartsch et al. |
| 8,697,902 B2 | 4/2014 | Mastroianni |
| 2004/0116713 A1 | 6/2004 | Beller et al. |
| 2006/0258874 A1 | 11/2006 | Bartsch et al. |
| 2009/0227801 A1 | 9/2009 | Ahlers et al. |
| 2011/0021804 A1 | 1/2011 | Mastroianni |
| 2011/0118499 A1 | 5/2011 | Mastroianni |
| 2011/0166376 A1 | 7/2011 | Mastroianni |
| 2011/0288327 A1 | 11/2011 | Mastroianni |

FOREIGN PATENT DOCUMENTS

| | | |
|---|---|---|
| DE | 199 53 058 A1 | 5/2001 |
| DE | 103 14 761 A1 | 10/2004 |

(Continued)

OTHER PUBLICATIONS

Oishi (Silicon(IV) Lewis Acids, in Lewis Acids in Organic Syth., 2000, ch. 9, p. 355-393).*

(Continued)

*Primary Examiner* — Robert Havlin
(74) *Attorney, Agent, or Firm* — Robert B. Furr, Jr.; Jeffrey A. Freeman

(57) ABSTRACT

The present invention relates to a process for producing compounds comprising at least one nitrile function by hydrocyanation of a compound comprising at least one non-conjugated unsaturation.

The invention proposes a process for producing compounds comprising at least one nitrile function by hydrocyanation of an organic compound comprising at least one non-conjugated unsaturation, comprising from 2 to 20 carbon atoms, by reaction with hydrogen cyanide in the presence of a catalytic system comprising a complex of nickel having the oxidation state of zero with at least one organophosphorus ligand chosen from the group comprising organophosphites, organophosphonites, organophosphinites and organosphosphines and a cocatalyst of the Lewis acid type.

6 Claims, No Drawings

(56) References Cited

FOREIGN PATENT DOCUMENTS

| | | |
|---|---|---|
| EP | 0336314 A | 10/1989 |
| FR | 1 529 134 A1 | 5/1968 |
| FR | 2 069 411 A1 | 9/1971 |
| FR | 2 523 974 A1 | 9/1983 |
| FR | 2 830 530 A1 | 4/2003 |
| FR | 2 849 027 A1 | 6/2004 |
| FR | 2 854 892 A1 | 11/2004 |
| FR | 2 845 379 A1 | 4/2009 |
| WO | WO 96/22968 | 8/1996 |
| WO | WO 99/06355 A1 | 2/1999 |
| WO | WO 99/06356 A1 | 2/1999 |
| WO | WO 99/06357 A1 | 2/1999 |
| WO | WO 99/52632 A1 | 10/1999 |
| WO | WO 99/62855 A1 | 12/1999 |
| WO | WO 99/64155 A1 | 12/1999 |
| WO | WO 99/65506 A1 | 12/1999 |
| WO | WO 01/36429 A1 | 5/2001 |
| WO | WO 02/13964 A1 | 2/2002 |
| WO | WO 02/30854 A2 | 4/2002 |
| WO | WO 02/053527 A1 | 7/2002 |
| WO | WO 03/011457 A1 | 2/2003 |
| WO | WO 03/031392 A1 | 4/2003 |
| WO | WO 03/068729 A1 | 8/2003 |
| WO | WO 2004/007432 A1 | 1/2004 |
| WO | WO 2004/007434 A1 | 1/2004 |
| WO | WO 2004/060855 A1 | 7/2004 |
| WO | WO 2004/065352 A1 | 8/2004 |
| WO | WO 2004/087314 A1 | 10/2004 |
| WO | WO 2009/092639 A1 | 7/2009 |

OTHER PUBLICATIONS

"Aliphatic Compounds" IUPAC Compendium of Chemical Terminology 2nd Edition (1997).*
Hirano et al. (Chem. Commun., 2008, 3234-3241).*
International Search Report dated Jan. 25, 2010 issued in PCT/EP2009/062896.
Gibson et al., "Formation and Unexpected Catalytic Reactivity of Oranoaluminum Boryloxides," *Inorg. Chem.*, 40(5): 826-827 (2001).
Serwatowski et al., "New Tetrameric Alkylmetal Boryloxides [($\mu^3$-$R_2BO$)MR']$_4$ of Zinc and Cadmium with Heterocubane Structure," *Inorg. Chem.*, 38(22): 4937-4941 (1999).
Serwatowski et al., "Diverse Reactivity of Dialkylaluminum Dimesitylboryloxides [($\mu$-$Mes_2BO$)$AlR_2$]$_2$ Synthetic and Structural Study," *Inorg. Chem.*, 39(25): 5763-5767 (2000).
International Search Report dated Jan. 25, 2010, issued in PCT/EP2009/062896.
International Search Report (PCT/ISN210) issued on May 25, 2010, by European Patent Office as the International Searching Authority for International Application No. PCT/EP2010/050521.
International Search Report dated Dec. 23, 2009 issued in PCT/EP2009/056916.
International Search Report dated Jul. 30, 2009, issued in PCT/EP 2009/050265.
International Search Report dated Aug. 10, 2009, issued in PCT/EP2009/056917.
Office Action mailed Jul. 5, 2012, in U.S. Appl. No. 12/864,101.
Office Action mailed Dec. 17, 2012, in U.S. Appl. No. 12/864,101.
Office Action mailed Jun. 28, 2013, in U.S. Appl. No. 12/864,101.
Final Office Action mailed Mar. 21, 2014, in U.S. Appl. No. 12/864,101.
Advisory Action mailed Jul. 30, 2014, in U.S. Appl. No. 12/864,101.
Office Action mailed Oct. 24, 2014, in U.S. Appl. No. 12/864,101.
Office Action mailed May 9, 2013, in U.S. Appl. No. 13/123,721.
Final Office Action mailed Nov. 14, 2013, in U.S. Appl. No. 13/123,721.
Office Action mailed Jun. 6. 2014, in U.S. Appl. No. 13/123,721.
Final Office Action mailed Nov. 17, 2014, in U.S. Appl. No. 13/123,721.
Office Action mailed Oct. 25, 2013, in U.S. Appl. No. 13/146,610.
Final Office Action mailed Jul. 17, 2014, in U.S. Appl. No. 13/146,610.

* cited by examiner

PROCESS FOR PRODUCING COMPOUNDS COMPRISING NITRILE FUNCTIONS

This application is the United States national phase of PCT/EP2009/062896, filed Oct. 5, 2009, and designating the United States (published in the French language on Apr. 29, 2010, as WO 2010/046226 A1; the title and abstract were also published in English) and claims priority under 35 U.S.C. §119 of FR 0805821, filed Oct. 21, 2008, each hereby expressly incorporated by reference in its entirety and each assigned to the assignee hereof.

The present invention relates to a process for producing compounds comprising at least one nitrile function by hydrocyanation of a compound comprising at least one non-conjugated unsaturation.

It relates more particularly to a production process implementing the reaction of hydrogen cyanide with an organic compound comprising a non-conjugated unsaturation in the presence of a catalytic system comprising nickel having the oxidation state of zero (hereinafter referred to as Ni(0)) with at least one organophosphorus ligand and a cocatalyst belonging to the Lewis acid family.

Such processes have been known for many years and are exploited industrially, in particular for the production of a major chemical intermediate, adiponitrile. This compound is in particular used in the production of hexamethylenediamine, which is an important monomer for the production of polyamides and also an intermediate in the synthesis of diisocyanate compounds.

Thus, the company DU PONT DE NEMOURS has developed and exploited a process for producing adiponitrile by double hydrocyanation of butadiene. This reaction is generally catalysed by a catalytic system comprising a complex of nickel(0) with organophosphorus ligands. This system also comprises a cocatalyst, in particular in the second hydrocyanation step, i.e. hydrocyanation of unsaturated compounds comprising a nitrile function, such as pentenenitriles to dinitrile compounds.

Many cocatalysts have been proposed in patents and are generally compounds belonging to the Lewis acid family. One of the roles of this cocatalyst or promoter is to limit the production of by-products and therefore to promote the formation of linear dinitrile compounds compared with the formation of branched dinitriles.

Thus, many metal halides, such as zinc chloride, zinc bromide, stannous chloride or stannous bromide, have already been proposed, for example in U.S. Pat. No. 3,496,217. Zinc chloride is the preferred cocatalyst.

Organic boron compounds such as triphenyl boron or compounds comprising two boron atoms, as described in U.S. Pat. Nos. 3,864,380 and 3,496,218, or organic tin compounds as in U.S. Pat. No. 4,874,884, have also been proposed.

These cocatalysts have different properties and make it possible to obtain selectivities for different linear dinitriles such as adiponitrile. Some of these cocatalysts have drawbacks associated with the difficulty in extracting them from the reaction medium or with the possibility and ease of extracting the catalytic system or the nickel(0) ligand in the presence of this cocatalyst, in order to recycle it.

There still exists a need to find new cocatalysts for obtaining selectivities for linear dinitriles that are of acceptable levels and easy to use.

One of the aims of the present invention is to provide a new family of compatible cocatalysts which give adiponitrile-selectivity levels that are suitable in the pentenenitrile hydrocyanation reaction.

To this effect, the invention provides a process for producing compounds comprising at least one nitrile function by hydrocyanation of an organic compound comprising at least one non-conjugated unsaturation, comprising from 2 to 20 carbon atoms, by reaction with hydrogen cyanide in the presence of a catalytic system comprising a complex of nickel having the oxidation state of zero with at least one organophosphorus ligand chosen from the group comprising organophosphites, organophosphonites, organophosphinites and organophosphines and a cocatalyst, characterized in that the cocatalyst is an organometallic compound corresponding to general formula I:

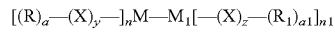

in which:
M, $M_1$, which may be identical or different, represent an element chosen from the group comprising the following elements: B, Si, Ge, Sn, Pb, Mo, Ni, Fe, W and Cr, R, $R_1$, which may be identical or different, represent an aliphatic radical or a radical comprising an aromatic or cycloaliphatic ring, which is substituted or unsubstituted, and which may or may not be bridged, or a halide radical, X representing an oxygen, nitrogen, sulphur or silicon atom, y and z are integers, which may or may not be identical, equal to 0 or 1, n and $n_1$ are integers equal to the valency of the elements M, $M_1$ reduced by 1, a and a1 are integers, which may or may not identical, equal to the valency of the element X reduced by 1 if y and z are equal to 1, or equal to 1 if y and z are equal to 0.

Advantageously, R and R1, which may be identical or different, represent an aromatic, aliphatic or cycloaliphatic radical, which is substituted or unsubstituted, and which may or may not be bridged, or a halide radical.

In the formula above, the bond between the elements M and $M_1$ is symbolized by a covalent bond. However, said bond may be multiple, depending on the nature of the elements M and $M_1$.

In the formula above, a is equal to the valency of the element X reduced by 1 if y is equal to 1, and a is equal to 1 if y is equal to 0. Similarly, a1 is equal to the valency of the element X reduced by 1 is z is equal to 1, and a1 is equal to 1 if z is equal to 0.

In the formula above, the R radicals may be identical or different. Similarly the $R_1$ radicals may be identical or different.

According to one preferred characteristic of the invention, the cocatalyst is advantageously chosen from the group of the following compounds:
 bis(neopentylglycolato)diboron (RN CAS 201733-56-4)
 bis(hexyleneglycolato)diboron (RN CAS 230299-21-5)
 bis(pinacolato)diboron (RN CAS 73183-34-3)
 tetrakis(pyrrolinido)diboron (RN CAS 158752-98-8)
 hexamethyldisilane (RN CAS 1450-14-2)
 tetraphenyldimethyldisilane (RN CAS 1172-76-5)
 diphenyltetramethyldisilane (RN CAS 1145-98-8)
 tris(trimethylsilyl)silane (RN CAS 1873-77-4)
 tetrakis(trimethylsilyl)silane (RN CAS 4098-98-0)
 hexaphenyldisilane (RN CAS 1450-23-3)
 hexamethyldigermane (RN CAS 993-52-2)
 hexaethyldigermane (RN CAS 993-62-4)
 hexaphenyldigermane (RN CAS 2816-39-9)
 hexamethyldistannane (RN CAS 661-69-8)
 hexbutyldistannane (RN CAS 813-19-4)
 hexaphenyldistannane (RN CAS 1064-10-4)

triphenylstannyldimethylphenylsilane (RN CAS 210362-76-8)

triphenylgermanyltriphenylstannane (RN CAS 13904-13-7)

hexaphenyldilead (RN CAS 3124-01-4)

cyclopentadienyliron dicarbonyl dimer (RN CAS 38117-54-3)

cyclopentadienylchromium dicarbonyl dimer (RN CAS 37299-12-0)

cyclopentadienylnickel carbonyl dimer (RN CAS 12170-92-2)

cyclopentadienyltungsten tricarbonyl dimer (RN CAS 12566-66-4)

methylcyclopentadienylmolybdenum tricarbonyl dimer (RN CAS 33056-03-0).

The cocatalysts of the invention are compounds which are described in the literature, as is the process for producing them. The registration number RN CAS is given solely for information purposes. Most of these compounds are commercially available.

In one preferred embodiment of the invention, the catalytic system of the invention contains a cocatalyst in accordance with the invention in a molar ratio of cocatalyst relative to the number of nickel atoms of between 0.01 and 50, and preferably between 0.1 and 10.

The catalytic system of the invention comprises a complex of nickel(0) with at least one organophosphorus compound, preferably a monodentate compound such as triphenylphosphite or tritolylphosphite, described for example in U.S. Pat. No. 3,496,215, DE19953058, FR1529134, FR2069411, U.S. Pat. Nos. 3,631,191, 3,766,231 or FR2523974, or a bidentate compound such as the organophosphite compounds described in Patents WO9906355, WO9906356, WO9906357, WO9906358, WO9952632, WO9965506, WO9962855, U.S. Pat. No. 5,693,843, WO961182, WO9622968, U.S. Pat. No. 5,981,772, WO0136429, WO9964155, WO0213964 and U.S. Pat. No. 6,127,567.

It is also possible to use complexes of nickel(0) with monodentate or bidentate organophosphine compounds as described in Patents WO02/30854, WO02/053527, WO03/068729, WO04/007435, WO04/007432, FR2845379 and WO2004/060855, and more particularly the trithienylphosphine described in the unpublished French application no. 0800381 and the DPPX described in Patent WO2003/031392.

Similarly, the catalytic system of the invention may comprise a complex of nickel(0) with monodentate or bidentate organophosphorus compounds belonging to the organophosphonite or organophosphinite family.

It is also possible to use the cocatalysts of the invention with a nickel(0) complex obtained with a mixture of organophosphite monodentate ligand and of bidentate ligand chosen from the families of compounds belonging to the organophosphites, organophosphonites, organophosphinites or organophosphines, as described in Patents WO03/011457 and WO2004/065352.

The description of the hydrocyanation process is given in several patents, including those mentioned above, and also in the articles by C. A. Tolman published in the reviews Organometallics 3 (1984) 33, Advances in Catalysis (1985) 33-1 and Journal of Chemical Education (1986) vol 63, no. 3, pages 199-201.

Briefly, the process for producing compounds comprising at least one nitrile function, and more particularly dinitrile compounds such as adiponitrile, consists in reacting, in a first step, a diolefin such as 1,3-butadiene with hydrogen cyanide, generally in the absence of solvent and in the presence of a catalytic system. The reaction is carried out under pressure so as to be in a liquid medium. The unsaturated nitrile compounds are separated by successive distillations. The linear nitrile compounds, such as pentenenitriles, are fed into a second hydrocyanation step.

Advantageously, the nonlinear unsaturated nitriles obtained in the first step are subjected to an isomerization step in order to convert them to linear unsaturated nitriles, which are also introduced into the second hydrocyanation step.

In the second hydrocyanation step, the linear unsaturated nitriles are reacted with hydrogen cyanide in the presence of a catalytic system.

The dinitrile compounds formed are separated by successive distillations after extraction of the catalytic system from the reaction medium. Several processes for extracting the catalytic system are described, for example, in U.S. Pat. No. 3,773,809, 4,082,811, 4,339,395 and 5,847,191. Generally, the catalytic system can be separated from the reaction medium by separation into two phases by settling out, obtained by control of the ratios between the mononitrile compounds and the dinitrile compounds contained in the medium. This separation can be improved by the addition of ammonia. It is also possible to precipitate the catalytic system in order to recover it and recycle it, or to use a nonpolar solvent for extracting the catalytic system and separating it from the nitrile products.

The temperature conditions for these various steps are between 10 and 200° C.

The catalytic systems used in the first and second hydrocyanation steps and also in the isomerization step are generally similar, i.e. they contain an identical nickel(0) complex. However, the ratio between the number of nickel atoms and the number of ligand molecules may be different in each of these steps, and also the concentration of the catalytic system in the medium.

Preferably, the cocatalyst is present only in the catalytic system used for the second hydrocyanation step. However, it may also be present in the isomerization step.

The characteristics and performance levels of the process and therefore of the catalytic system used are determined and illustrated by the degree of conversion (DC) of the compound introduced, in particular of the unsaturated mononitrile introduced in the second step, and by the linearity with respect to linear dinitriles produced, i.e. the number of moles of linear dinitriles relative to the number of moles of dinitriles formed. In the case of the production of adiponitrile, the linearity corresponds to the percentage of moles of adiponitrile (AdN) obtained relative to the numbers of moles of dinitriles formed (AdN+ESN+MGN).

The invention will be illustrated more clearly by means of the examples given below, only by way of indication, relating to the production of adiponitrile by hydrocyanation of 3-pentenenitrile. In these examples, the 3-pentenenitrile used is a compound marketed by Aldrich.

In these examples, the following abbreviations are used:
Cod: cyclooctadiene
3PN: 3-pentenenitrile
AdN: adiponitrile
ESN: ethylsuccinonitrile
MGN: methylglutaronitrile
TTP: tri-para-tolylphosphite
DPPX: bis(diphenylphosphinomethyl)-1,2-benzene
DC(Y): degree of conversion of the product to be hydrocyanated Y, corresponding to the ratio of the number of converted moles of Y to the number of initial moles of Y
linearity (L): ratio of the number of moles of AdN formed to the number of moles of dinitriles formed (sum of the moles of AdN, ESN and MGN)

The compounds of formula I used in the examples below are commercially available.

EXAMPLE 1

Hydrocyanation of 3-PN so as to Give AdN

The general procedure used is the following:
The following are loaded successively, under an argon atmosphere, into a 60 ml glass tube of Schott type, equipped with a septum stopper:
- the ligand [5 molar equivalents of ligand per atom of Ni if the ligand is a monodentate such as TTP or trithienylphosphine, or 2.5 molar equivalents of ligand per atom of Ni if the ligand is bidentate, such as DPPX],
- 1.21 g (15 mmol, 30 equivalents) of anhydrous 3PN,
- 138 mg (0.5 mmol, 1 equivalent) of Ni(Cod)$_2$,
- Lewis acid (see the indications in Table I below for the nature and the amount).

The mixture is brought to 70° C. with stirring. Acetone cyanohydrin, an HCN generator, is injected into the reaction medium via a syringe driver with a flow rate of 0.45 ml per hour. After injecting for 3 hours, the syringe driver is stopped. The mixture is cooled to ambient temperature, diluted with acetone and analysed by gas chromatography.

The cocatalysts used in the examples are listed below:

cocatalyst A: bis(pinacolato)diboron (RN CAS: 73183-34-3)

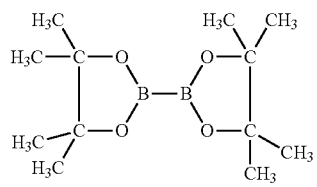

cocatalyst B: hexaethyldigermanium(IV) (RN CAS: 993-62-4)

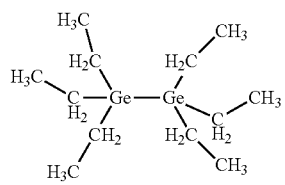

cocatalyst C: hexabutyldistannane (RN CAS 813-19-4)

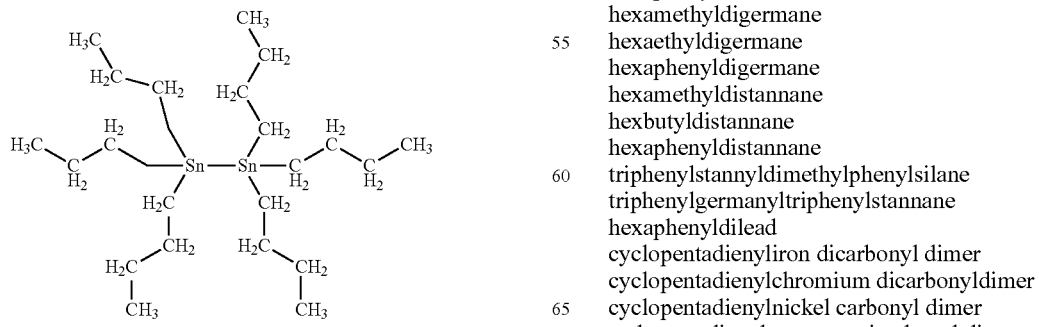

cocatalyst D: diphenyltetramethyldisilane (RN CAS 1145-98-8)

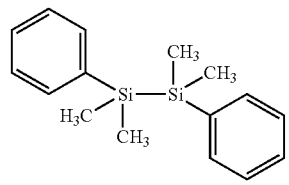 [SMILES: C[Si](C)(c1ccccc1)[Si](C)(C)c1ccccc1]

The results are given in Table I below.

TABLE I

Examples 1 to 11 which form part of the invention

| Example | Ligand | Lewis acid | Ni/Lewis acid (molar) | DC (3PN) | Linearity |
|---|---|---|---|---|---|
| 1 | TTP | A | 1/1 | 4.8 | 72.8 |
| 2 | TTP | B | 1/1 | 5.7 | 72.4 |
| 3 | TTP | C | 1/1 | 6.2 | 73.2 |
| 4 | TTP | D | 1/0.5 | 1.4 | 67.0 |
| 5 | DPPX | A | 1/0.5 | 17.0 | 93.7 |
| 6 | DPPX | B | 1/0.5 | 19.1 | 74.8 |
| 7 | DPPX | C | 1/0.5 | 21.7 | 82.9 |
| 8 | DPPX | D | 1/0.5 | 22.7 | 79.5 |
| 9 | Tri(2-thienyl)phosphine | A | 1/1 | 14.0 | 69.6 |
| 10 | Tri(2-thienyl)phosphine | B | 1/1 | 17.0 | 76.4 |
| 11 | Tri(2-thienyl)phosphine | C | 1/1 | 32.1 | 82.8 |

The invention claimed is:
1. A process for producing compounds comprising at least one nitrile function, the process comprising hydrocyanating an organic compound comprising at least one non-conjugated unsaturation and comprising from 2 to 20 carbon atoms, by reacting said organic compound with hydrogen cyanide in the presence of a catalytic system comprising a complex of nickel having an oxidation state of zero with at least one organophosphorus ligand selected from the group consisting of organophosphites, organophosphonites, organophosphinites and organophosphines and a cocatalyst, wherein the cocatalyst is selected from the group consisting of:
bis(neopentylglycolato)diboron
bis(hexyleneglycolato)diboron
bis(pinacolato)dlboron
tetrakis(pyrrolinido)diboron
hexamethyldlsilane
tetraphenyldimethyldisilane
diphenyltetramethyldisilane
tris(trimethylsilyl)silane
tetrakis(trimethylsilyl)silane
hexaphenyldisilane
hexamethyldigermane
hexaethyldigermane
hexaphenyldigermane
hexamethyldistannane
hexbutyldistannane
hexaphenyldistannane
triphenylstannyldimethylphenylsilane
triphenylgermanyltriphenylstannane
hexaphenyldilead
cyclopentadienyliron dicarbonyl dimer
cyclopentadienylchromium dicarbonyldimer
cyclopentadienylnickel carbonyl dimer
cydopentadienyltungsten tricarbonyl dimer; and
methylcyclopentadlenylmolybdenum tricarbonyl dimer.

2. The process according to claim 1, wherein the catalytic system comprises a molar ratio of cocatalyst relative to moles of Ni of between 0.1 and 10.

3. The process according to claim 1, wherein the organophosphorus ligand is selected from the group consisting of monodentate organophosphorous compounds and bidentate organophosphorus compounds.

4. The process according to claim 1, wherein the organic compounds is a pentenenitrile compound.

5. The process according to claim 4, wherein the compounds comprising at least one nitrile function are adiponitrile, methylglutaronitrile or succinonitrile.

6. The process according to claim 1, wherein the at least one organophosphorus ligand is tritolyl phosphite, bis(diphenylphosphinomethyl)-1,2-benzene or tris(2-thienyl)phosphine.

* * * * *